(12) United States Patent
Seibel et al.

(10) Patent No.: US 8,212,884 B2
(45) Date of Patent: Jul. 3, 2012

(54) SCANNING BEAM DEVICE HAVING DIFFERENT IMAGE ACQUISITION MODES

(75) Inventors: Eric J. Seibel, Seattle, WA (US); Richard S. Johnston, Sammamush, WA (US)

(73) Assignee: University of Washington, Seattle, WA (US)

( * ) Notice: Subject to any disclaimer, the term of this patent is extended or adjusted under 35 U.S.C. 154(b) by 1442 days.

(21) Appl. No.: 11/805,286

(22) Filed: May 22, 2007

(65) Prior Publication Data

US 2008/0291597 A1 Nov. 27, 2008

(51) Int. Cl.
*H04N 5/225* (2006.01)

(52) U.S. Cl. ............... 348/220.1; 348/206; 348/208.16; 348/221.1

(58) Field of Classification Search .............. 348/206, 348/208.16, 220.1, 221.1
See application file for complete search history.

(56) References Cited

U.S. PATENT DOCUMENTS

| | | |
|---|---|---|
| 3,470,320 A | 9/1969 | Pike et al. |
| 3,644,725 A | 2/1972 | Lochridge, Jr. |
| 4,206,495 A | 6/1980 | McCaslin |
| 4,234,788 A | 11/1980 | Palmer et al. |
| 4,264,208 A | 4/1981 | Haberl et al. |
| 4,710,619 A | 12/1987 | Haberl |
| 4,743,283 A | 5/1988 | Borsuk |
| 4,768,513 A | 9/1988 | Suzuki |
| 4,770,185 A | 9/1988 | Silverstein et al. |
| 4,782,228 A | 11/1988 | Westell |
| 4,821,117 A | 4/1989 | Sekiguchi et al. |
| 4,831,370 A | 5/1989 | Smoot |
| 4,872,458 A | 10/1989 | Kanehira et al. |
| 4,948,219 A | 8/1990 | Seino et al. |
| 4,963,018 A | 10/1990 | West |
| 5,081,350 A | 1/1992 | Iwasaki et al. |
| 5,172,685 A | 12/1992 | Nudelman |
| 5,178,130 A | 1/1993 | Kaiya |
| 5,185,835 A | 2/1993 | Vial et al. |
| 5,276,563 A * | 1/1994 | Ogawa ..................... 386/224 |
| 5,315,383 A | 5/1994 | Yabe et al. |

(Continued)

FOREIGN PATENT DOCUMENTS

EP 1077360 2/2001

(Continued)

OTHER PUBLICATIONS

Aloisi et al., "Electronic Linearization of Piezoelectric Actuators and Noise Budget in Scanning Probe Microscopy", Review of Scientific Instruments, vol. 77, No. 7, Jul. 5, 2006, pp. 073701-1 through 073701-6.

(Continued)

*Primary Examiner* — Michael Won
(74) *Attorney, Agent, or Firm* — Blakely, Sokoloff, Taylor & Zafman LLP

(57) ABSTRACT

A method of one aspect may include monitoring movement of a scanning beam image acquisition device. Images may be acquired with the scanning beam image acquisition device using a first image acquisition mode when the monitoring indicates that the scanning beam image acquisition device is moving. Images may be acquired with the scanning beam image acquisition device using a second image acquisition mode when the monitoring indicates that the scanning beam image acquisition device is substantially still. The second image acquisition mode is different than the first image acquisition mode. In one aspect, the first mode has a relatively higher frame rate and relatively lower number of lines of image resolution than the second mode.

30 Claims, 8 Drawing Sheets

U.S. PATENT DOCUMENTS

| | | |
|---|---|---|
| 5,360,968 A | 11/1994 | Scott |
| 5,454,807 A | 10/1995 | Lennox et al. |
| 5,455,669 A | 10/1995 | Wetteborn |
| 5,459,570 A | 10/1995 | Swanson et al. |
| 5,557,444 A | 9/1996 | Melville et al. |
| 5,596,339 A | 1/1997 | Furness, III et al. |
| 5,627,922 A | 5/1997 | Koelman et al. |
| 5,664,043 A | 9/1997 | Donaldson et al. |
| 5,694,237 A | 12/1997 | Melville |
| 5,695,491 A | 12/1997 | Silverstein |
| 5,701,132 A | 12/1997 | Kollin et al. |
| 5,751,465 A | 5/1998 | Melville et al. |
| 5,784,098 A | 7/1998 | Shoji et al. |
| 5,822,073 A | 10/1998 | Yee et al. |
| 5,822,486 A | 10/1998 | Svetkoff et al. |
| 5,887,009 A | 3/1999 | Mandella et al. |
| 5,894,122 A | 4/1999 | Tomita |
| 5,903,397 A | 5/1999 | Melville et al. |
| 5,913,591 A | 6/1999 | Melville |
| 5,939,709 A | 8/1999 | Ghislain et al. |
| 5,969,871 A | 10/1999 | Tidwell et al. |
| 5,982,528 A | 11/1999 | Melville |
| 5,982,555 A | 11/1999 | Melville et al. |
| 5,991,048 A | 11/1999 | Karlson et al. |
| 5,995,264 A | 11/1999 | Melville |
| 6,046,720 A | 4/2000 | Melville et al. |
| 6,049,407 A | 4/2000 | Melville |
| 6,061,163 A | 5/2000 | Melville |
| 6,069,698 A | 5/2000 | Ozawa et al. |
| 6,069,725 A | 5/2000 | Melville |
| 6,097,353 A | 8/2000 | Melville et al. |
| 6,154,321 A | 11/2000 | Melville et al. |
| 6,157,352 A | 12/2000 | Kollin et al. |
| 6,166,841 A | 12/2000 | Melville |
| 6,191,761 B1 | 2/2001 | Melville et al. |
| 6,204,832 B1 | 3/2001 | Melville et al. |
| 6,220,711 B1 | 4/2001 | Melville et al. |
| 6,243,186 B1 | 6/2001 | Melville et al. |
| 6,257,727 B1 | 7/2001 | Melville |
| 6,263,234 B1 | 7/2001 | Engelhardt et al. |
| 6,281,862 B1 | 8/2001 | Tidwell et al. |
| 6,285,505 B1 | 9/2001 | Melville et al. |
| 6,288,816 B1 | 9/2001 | Melville et al. |
| 6,291,819 B1 | 9/2001 | Hartley |
| 6,294,775 B1 | 9/2001 | Seibel et al. |
| 6,317,548 B1 | 11/2001 | Rockwell et al. |
| 6,369,953 B2 | 4/2002 | Melville et al. |
| 6,388,641 B2 | 5/2002 | Tidwell et al. |
| 6,411,838 B1 | 6/2002 | Nordstrom et al. |
| 6,441,359 B1 | 8/2002 | Cozier et al. |
| 6,452,632 B1 * | 9/2002 | Umeda et al. ............... 348/294 |
| 6,492,962 B2 | 12/2002 | Melville et al. |
| 6,535,183 B2 | 3/2003 | Melville et al. |
| 6,538,625 B2 | 3/2003 | Tidwell et al. |
| 6,560,028 B2 | 5/2003 | Melville et al. |
| 6,563,105 B2 | 5/2003 | Seibel et al. |
| 6,581,445 B1 | 6/2003 | Weiss |
| 6,700,552 B2 | 3/2004 | Kollin et al. |
| 6,734,835 B2 | 5/2004 | Tidwell et al. |
| 6,747,753 B1 | 6/2004 | Yamamoto |
| 6,832,724 B2 * | 12/2004 | Yavid et al. .................. 235/454 |
| 6,845,190 B1 | 1/2005 | Smithwick et al. |
| 6,850,673 B2 | 2/2005 | Johnston, II et al. |
| 6,856,712 B2 | 2/2005 | Fauver et al. |
| 6,867,753 B2 | 3/2005 | Chinthammit et al. |
| 6,930,703 B1 * | 8/2005 | Hubel et al. .................. 348/37 |
| 6,959,130 B2 | 10/2005 | Fauver et al. |
| 6,975,898 B2 | 12/2005 | Seibel |
| 6,977,631 B2 | 12/2005 | Melville et al. |
| 7,012,635 B2 * | 3/2006 | Umeda et al. ............. 348/208.4 |
| 7,068,878 B2 | 6/2006 | Crossman-Bosworth et al. |
| 7,123,790 B2 | 10/2006 | Rosman et al. |
| 7,159,782 B2 | 1/2007 | Johnston et al. |
| 7,184,150 B2 | 2/2007 | Qualing et al. |
| 7,189,961 B2 | 3/2007 | Johnston et al. |
| 7,212,230 B2 * | 5/2007 | Stavely ...................... 348/208.1 |
| 7,230,583 B2 | 6/2007 | Tidwell et al. |
| 7,252,236 B2 | 8/2007 | Johnston et al. |
| 7,277,819 B2 | 10/2007 | Marcus et al. |
| 7,583,293 B2 * | 9/2009 | Norskog .................... 348/218.1 |
| 7,683,940 B2 * | 3/2010 | Fleming ..................... 348/222.1 |
| 2001/0051761 A1 | 12/2001 | Khadem |
| 2001/0055462 A1 | 12/2001 | Seibel |
| 2002/0010384 A1 | 1/2002 | Shahidi et al. |
| 2002/0062061 A1 | 5/2002 | Kaneko et al. |
| 2002/0064341 A1 | 5/2002 | Fauver et al. |
| 2002/0080359 A1 | 6/2002 | Denk et al. |
| 2002/0093467 A1 | 7/2002 | Tidwell et al. |
| 2002/0093563 A1 | 7/2002 | Cline et al. |
| 2002/0097498 A1 | 7/2002 | Melville et al. |
| 2002/0139920 A1 | 10/2002 | Seibel et al. |
| 2003/0004412 A1 | 1/2003 | Izatt et al. |
| 2003/0010825 A1 | 1/2003 | Schmidt et al. |
| 2003/0010826 A1 | 1/2003 | Dvorkis et al. |
| 2003/0016187 A1 | 1/2003 | Melville et al. |
| 2003/0025800 A1 * | 2/2003 | Hunter et al. ............. 348/208.13 |
| 2003/0048540 A1 | 3/2003 | Xie et al. |
| 2003/0142042 A1 | 7/2003 | Tidwell et al. |
| 2003/0169966 A1 | 9/2003 | Tokizaki |
| 2003/0202361 A1 | 10/2003 | Johnston et al. |
| 2004/0061072 A1 | 4/2004 | Gu et al. |
| 2004/0122328 A1 | 6/2004 | Wang et al. |
| 2004/0153030 A1 | 8/2004 | Novak |
| 2004/0196213 A1 | 10/2004 | Tidwell et al. |
| 2004/0212851 A1 | 10/2004 | Osakabe |
| 2004/0254474 A1 | 12/2004 | Seibel et al. |
| 2005/0020926 A1 | 1/2005 | Wiklof et al. |
| 2005/0025368 A1 | 2/2005 | Glukhosvsky |
| 2005/0085708 A1 | 4/2005 | Fauver et al. |
| 2005/0085721 A1 | 4/2005 | Fauver et al. |
| 2005/0174610 A1 | 8/2005 | Fukawa |
| 2005/0182295 A1 | 8/2005 | Soper et al. |
| 2005/0238277 A1 | 10/2005 | Wang et al. |
| 2006/0072189 A1 | 4/2006 | DiMarzio |
| 2006/0072843 A1 | 4/2006 | Johnston |
| 2006/0072874 A1 | 4/2006 | Johnston |
| 2006/0077121 A1 | 4/2006 | Melville et al. |
| 2006/0138238 A1 | 6/2006 | Johnston et al. |
| 2006/0149134 A1 | 7/2006 | Soper et al. |
| 2006/0186325 A1 | 8/2006 | Johnston et al. |
| 2006/0195014 A1 | 8/2006 | Seibel et al. |
| 2006/0226231 A1 | 10/2006 | Johnston et al. |
| 2006/0287647 A1 | 12/2006 | Torchia et al. |
| 2007/0081168 A1 | 4/2007 | Johnston et al. |
| 2007/0091426 A1 | 4/2007 | Johnston et al. |
| 2007/0129601 A1 | 6/2007 | Johnston et al. |
| 2007/0135693 A1 | 6/2007 | Melman et al. |
| 2007/0156021 A1 | 7/2007 | Morse et al. |
| 2007/0273930 A1 | 11/2007 | Berier et al. |
| 2008/0144998 A1 | 6/2008 | Melville et al. |
| 2008/0161648 A1 | 7/2008 | Karasawa |
| 2008/0291597 A1 * | 11/2008 | Seibel et al. ................... 361/241 |
| 2009/0156937 A1 * | 6/2009 | Sasaki et al. .................. 600/447 |
| 2010/0157037 A1 * | 6/2010 | Iketani et al. .................... 348/68 |
| 2011/0221913 A1 * | 9/2011 | Nagai et al. ................ 348/208.1 |

FOREIGN PATENT DOCUMENTS

| | | |
|---|---|---|
| EP | 1360927 | 11/2003 |
| EP | 1864606 | 12/2006 |
| GB | 2057709 | 4/1981 |
| GB | 2378259 | 2/2003 |
| JP | 08211313 | 8/1996 |
| WO | WO-9300551 | 1/1993 |
| WO | WO-01/74266 | 10/2001 |
| WO | WO-0174266 | 10/2001 |
| WO | WO-03019661 | 3/2003 |
| WO | WO-2004/040267 | 5/2004 |
| WO | WO-2004040267 | 5/2004 |
| WO | WO-2004068218 | 8/2004 |
| WO | WO-2005009513 | 2/2005 |
| WO | WO-2006004743 | 1/2006 |
| WO | WO-2006041452 | 4/2006 |
| WO | WO-2006041459 | 4/2006 |
| WO | WO-2006071216 | 7/2006 |
| WO | WO-2006096155 | 9/2006 |
| WO | WO-2006/106853 | 10/2006 |
| WO | WO-2006104489 | 10/2006 |

| | | |
|---|---|---|
| WO | WO-2006124800 | 11/2006 |
| WO | WO-2007018494 | 2/2007 |
| WO | WO-2007070831 | 6/2007 |
| WO | WO-2008/033168 | 3/2008 |

OTHER PUBLICATIONS

"PCT/US2007/015576 International Search Report", (Mar. 13, 2008), 4 pages.

Brown, Christopher M., et al., "Optomechanical design and fabrication of resonant microscanners for a scanning fiber endoscope", *Optical Engineering*, vol. 45, XP002469237, (Apr. 2006), pp. 1-10.

Smithwick, Y. J., et al., "An error space controller for a resonating fiber scanner: simulation and implementation", *Journal of Dynamic Systems, Measurement and Control*, Fairfiled, N.J., U.S., vol. 128, No. 4, XP009095153, ISSN:0022-0434, (Dec. 2006), pp. 899-913.

"PCT/US2007/009598 International Search Report", (Jan. 3, 2008), 3 pages.

Barhoum, Erek S., et al., "Optical modeling of an ultrathin scanning fiber endoscope, a preliminary study of confocal versus non-confocal detection", *Optics Express*, vol. 13, No. 19, (Sep. 8, 2005), pp. 7548-7562.

Brown, Christopher, et al., "A Novel Design for a Scanning Fiberoptic Endoscope", *Human Interface Technology Laboratory, University of Washington*, Seattle, WA 98195, Presented at SPIE's Regional Meeting on Optoelectronics, Photonics, and Imaging, (Nov. 1-2, 1999), 1 page.

Brown, Christopher M., et al., "Mechanical Design and Analysis for a Scanning Fiber Endoscope", *Proceedings of 2001 ASME Int'l Mechanical Engineering Congress and Exposition*, BED-vol. 51, (Nov. 11-16, 2001), 165-166.

Chen, Tailian, et al., "Experiment of Coalescence of Dual Bubbles on Micro Heaters", *Department of Mechanical Engineering, University of Florida*, Gainesville, FL 32611-6300. USA., Printed from the Internet Aug. 13, 2006, 1-10.

Fauver, Mark, et al., "Microfabrication of fiber optic scanners", (2002) *In Proceedings of Optical Scanning II, SPIE 4773*, pp. 102-110., 9 pages.

Johnston, Richard S., et al., "Scanning fiber endoscope prototype performance", *Optical Fibers and Sensors for Medical Applications II, Proc. SPIE*, vol. 4616, (Oct. 13, 2004), 173-179.

Seibel, Eric J., et al., "A full-color scanning fiber endoscope", *Optical Fibers and Sensors for Medical Diagnosis and Treatment Applications. Ed. I Gannot. Proc. SPIE* vol. 6083, (2006), 9-16.

Seibel, Eric J., et al., "Microfabricated optical fiber with microlens that produces large field-of-view, video rate, optical beam scanning for microendoscopy applications", *Optical Fibers and Sensors for Medical Applications III, Proceedings of SPIE* vol. 4957, (2003), 46-55.

Seibel, Eric J., et al., "Modeling optical fiber dynamics for increased efficiencies in scanning fiber applications", *Optical Fibers and Sensors for Medical Applications V, proceedings of SPIE* vol. 5691, (2005), 42-53.

Seibel, Eric J., et al., "P-37: Optical fiber scanning as a microdisplay source for a wearable low vision aid", *Society for Information Display SID* 2002, Boston, MA, (May 19-24, 2002), 1-4.

Seibel, Eric J., et al., "Prototype scanning fiber endoscope", *Optial Fibers and Sensors for Medical Applications II, Proc. of SPIE*, vol. 4616, (2002), 1-7.

Seibel, Eric J., et al., "Single fiber flexible endocope: general design for small size, high resoljution, and wide field of view", *Human Interface Technology Laboratory, College of Engineering, University of Washington*, Seattle, WA, Proceedings of the SPIE, Biomonitoring and Endoscopy Technologies 4158, (2001), 11 pages.

Seibel, Eric J., et al., "Ultrathin laser scanning bronchoscope and guidance system for the peripheral lung", *11th World Conference on Lung Cancer*, (2005), p. 178.

Seibel, Eric J., et al., "Unique Features of Optical Scanning, Single Fiber Endoscopy", *Lasers in Surgery and Medicine 30*, (2002), 177-183.

Seibel, Eric, et al., "Unique Features of Scanning Fiber Optical Endopscopy", 2000 *Annual Fall Meeting Abstracts T4.57*, (2000), 1.

Smithwick, Quinn Y., et al., "54.3: Modeling and Control of the Resonant Fiber Scanner for Laser Scanning Display or Acquisition", *Department of Aeronautics and Astronautics, University of Washington*, Seattle, WA SID 03 Digest, (2003), 1455-1457.

Smithwick, Quinn Y., et al., "A Nonlinear State-Space Model of Resonating Single Fiber Scanner for Tracking Control: Theory and Experiment", *Transactions fo the ASME*, vol. 126, (Mar. 2004), 88-101.

Smithwick, Quinn Y., et al., "Control Aspects of the Single Fiber Scanning Endoscope", (2001) *SPIE Optical Fibers and Sensors for Medical Applications*, 4253, 176-188., 15 pages.

Smithwick, Quinn Y., et al., "Depth Enhancement using a Scanning Fiber Optical Endoscope", *Department of Aeronautics, Human Interface Technology Laboratory, University of Washington*, Seattle, Washington, Optical Biopsy IV, Proc. SPIE 4613, (2002), 12 pages.

Tuttle, Brandon W., et al., "Delivery of therapeutic laser light using a singlemode silica fiber for a scanning fiber endoscope system", *Optical Fibers and Sensors for Medical Diagnostics and Treatment Applications VI, Proc. of SPIE* vol. 6083,, (2006), 608307-1 to 608307-12.

Wang, Wei-Chih, et al., "Development of Optical Waveguide Cantilever Scanner", *Opto-Ireland 2002: Optics and Photonics Technologies and Applications, Proceedings of SPIE* vol. 4876 (2003), 72-83.

Wang, Wei-Chih, et al., "Micromachined opital waveguide cantilever as a resonant optical scanner", *Department of Mechanical Engineering, University of Washington*, Seattle, WA 98195, *Sensors and Actuators A 102*, (2002), 165-175.

* cited by examiner

FIRST SPIRAL FOR FIRST
IMAGE ACQUISITION MODE
*1268*

SECOND SPIRAL FOR SECOND
IMAGE ACQUISITION MODE
*1269*

SCANNING BEAM DEVICE HAVING DIFFERENT IMAGE ACQUISITION MODES

BACKGROUND

1. Field

Embodiments of the invention relate to image acquisition. In particular, embodiments of the invention relate to scanning beam image acquisition devices.

2. Background Information

Scanning beam image acquisition devices are known in the arts. One type of scanning beam image acquisition device is a scanning fiber endoscope. Images may be acquired with the scanning beam image acquisition devices both while they are moving and while they are still. The same frame rate and number of lines of image resolution may be used to acquire images both while they are moving and while they are still. However the inventors recognize that there are certain drawbacks with this approach.

BRIEF DESCRIPTION OF THE SEVERAL VIEWS OF THE DRAWINGS

The invention may best be understood by referring to the following description and accompanying drawings that are used to illustrate embodiments of the invention. In the drawings.

DETAILED DESCRIPTION

In the following description, numerous specific details are set forth. However, it is understood that embodiments of the invention may be practiced without these specific details. In other instances, well-known circuits, structures and techniques have not been shown in detail in order not to obscure the understanding of this description.

Figure 1:
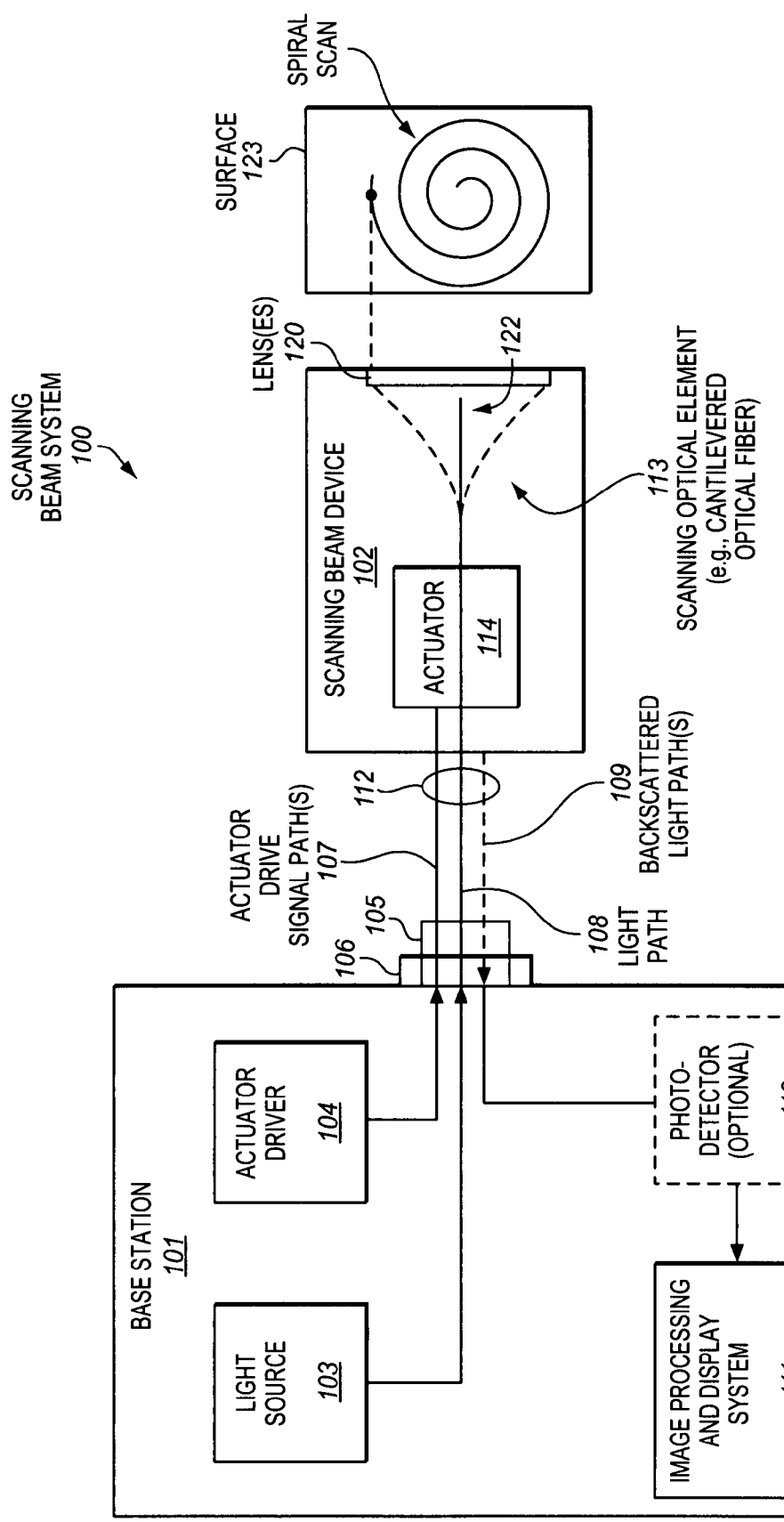
FIG. 1 is a block diagram of an example scanning beam image acquisition system, according to embodiments of the invention.

FIG. 1 is a block diagram of an example scanning beam image acquisition system 100, according to embodiments of the invention. In various embodiments of the invention, the scanning beam image acquisition system may take the form of a scanning beam endoscope, scanning beam borescope, scanning beam microscope, other type of scanning beam scope, scanning beam bar code reader, or other scanning beam image acquisition device known in the art. As will be discussed further below, one particular type of scanning beam device is a scanning fiber device.

As is known, endoscopes represent instruments or devices to be inserted into a patient to look inside a body cavity, lumen, or otherwise look inside the patient. Examples of suitable types of endoscopes include, but are not limited to, bronchoscopes, colonoscopes, gastroscopes, duodenoscopes, sigmoidoscopes, thoracoscopes, ureteroscopes, sinuscopes, boroscopes, and thorascopes, to name just a few examples.

The scanning beam image acquisition system has a two-part form factor that includes a base station 101 and a scanning beam image acquisition device 102. The scanning beam image acquisition device is electrically and optically coupled with the base station through one or more cables 112. In particular, the cable includes a connector 105 to connect with a corresponding connector interface 106 of the base station.

The terms "coupled" and "connected," along with their derivatives, are used herein. These terms are not intended as synonyms for each other. Rather, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still co-operate or interact with each other physically, electrically, or optically.

The base station includes a light source 103 to provide light to the scanning beam image acquisition device through a light path 108. Examples of suitable light sources include, but are not limited to, lasers, laser diodes, vertical cavity surface-emitting lasers (VCSELs), light-emitting diodes (LEDs), other light emitting devices known in the arts, and combinations thereof. In various example embodiments of the invention, the light source may include a red light source, a blue light source, a green light source, an RGB light source, a white light source, an infrared light source, an ultraviolet light source, a high intensity therapeutic laser light source, or a combination thereof. Depending on the particular implementation, the light source may emit a continuous stream of light, modulated light, or a stream of light pulses.

The base station also includes an actuator driver 104 to provide electrical signals, referred to herein as actuator drive signals, to the scanning beam image acquisition device through an actuator drive signal path 107. The actuator driver may be implemented in hardware (for example a circuit), software (for example a routine, program, or other set of machine-executable instructions), or a combination of hardware and software.

In one or more embodiments of the invention, the actuator driver may include one or more look-up tables or other data structures stored in a memory that may provide actuation drive signal values. Alternatively, the actuator driver may include a processor executing software, an ASIC, or other circuit to compute the actuation drive signal values in real time. As another option, computation may be used to interpolate between stored values.

In one aspect, the actuation drive signal values may optionally be ideal values that are adjusted based on calibration. One suitable type of calibration is described in U.S. Patent Application 20060072843, entitled "REMAPPING METHODS TO REDUCE DISTORTIONS IN IMAGES", by Richard S. Johnston. Other calibration approaches are also suitable.

The actuator driver may cycle through the lookup tables or computations providing the values. In some cases, the resulting values may be digital and may be provided to a digital-to-analog converter of the actuator driver. The actuator driver may also include one or more amplifiers to amplify the analog version of the actuator drive signals. These are just a few illustrative examples of suitable actuator drivers.

Refer now to the scanning beam image acquisition device 102. The illustrated scanning beam device is a scanning fiber device, although the scope of the invention is not so limited. The scanning fiber device includes a single cantilevered optical fiber 113 and an actuator 114 to actuate or move the cantilevered optical fiber. Examples of suitable types of actuators include, but are not limited to, piezoelectric tubes, Electroactive Polymer (EAP) tubes, other actuator tubes, other piezoelectric actuators, other EAP actuators, magnetic actuators, electromagnetic actuators, electrostatic actuators, sonic actuators, electroacoustic actuators, electromechanical actuators, microelectromechanical systems (MEMS), and other transducers capable of moving the cantilevered optical fiber.

The actuator may receive the actuator drive signals. The actuator may actuate or move the cantilevered optical fiber based on, and responsive to, the received actuator drive signals. In embodiments of the invention, the actuator drive signals may cause the actuator to move the cantilevered optical fiber in a two-dimensional scan. Examples of suitable two-dimensional scans include, but are not limited to, spiral scan patterns (whether or not they are circular or oval), propeller patterns, Lissajous scan patterns, raster scan patterns, and combinations thereof.

The cantilevered optical fiber may receive the light from the light source. The light may be emitted from, or otherwise directed through, a distal end or tip 122 of the cantilevered optical fiber, while the optical fiber is moved in the scan. The emitted light may be passed through one or more lenses 120 to generate a focused beam or illumination spot that may be moved across a surface 123 in the scan. In the illustration, a spiral scan pattern is shown and a dot shows a position of the illumination spot at a particular point in time during the scan.

The scanning beam device may be used to acquire an image of the surface. In acquiring the image of the surface, the scanning beam device may scan the illumination spot through the lens system and over the surface in the scan. Backscattered light may be captured in time series and used to construct an image. A greater number of spiral windings or other "lines" of the scan generally provides a greater number of lines of image resolution and generally better image quality. Also, a greater the number of spiral windings or other "lines" of the scan generally takes more time to complete the scan.

Different ways of collecting the backscattered light are possible. As shown, one or more optical fibers, or other backscattered light paths 109, may optionally be included to collect and convey backscattered light back to one or more optional photodetectors 110 of the base station. Alternatively, the scanning beam device may optionally include photodetectors proximate a distal tip thereof. The base station may also include an image processing and display system 111 to generate and display images based on light detected by the photodetectors. The display system may either be built into the base station or may be an external device coupled with the base station.

A simplified base station has been shown and described in order to avoid obscuring the description. It is to be appreciated that the base station may include other components. Representative components that may be included in the base station include, but are not limited to, a power source, a user interface, a memory, and the like. Furthermore, the base station may include supporting components like clocks, amplifiers, digital-to-analog converters, analog-to-digital converters, and the like.

Additionally, a scanning fiber device has been shown and described in order to illustrate certain concepts, although the scope of the invention is not limited to just scanning fiber devices. For example, other scanning beam devices are possible in which the optical fiber is replaced by a micromachined optical waveguide, or other non-fiber optical waveguide. As another example, a scanning beam device may include a mirror or other reflective device that may be moved by an actuator to scan a reflected beam. As yet another example, a scanning beam device may include a lens or other focusing device that may be moved by an actuator to scan a focused beam. Still other scanning beam devices are possible that include multiple such optical elements that may be moved relative to each other to scan the beam.

The scanning beam system just described has a two-part form factor. The scanning beam device is generally relatively small and maneuverable compared to the base station. As will be explained next, images may be acquired with the scanning beam device both when it is being navigated or otherwise moved, and when it is substantially still.

Figure 2:
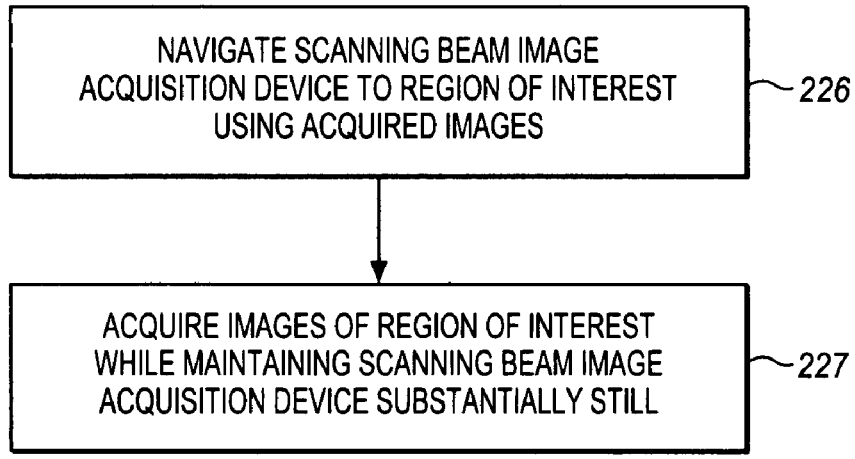
FIG. 2 is a block flow diagram of an example method of using a scanning beam image acquisition device, according to embodiments of the invention.

FIG. 2 is a block flow diagram of an example method 225 of using a scanning beam image acquisition device, according to embodiments of the invention.

At block 226, the scanning beam image acquisition device may be navigated to a region of interest using images acquired with the scanning beam image acquisition device. As one example, a scanning beam endoscope may be inserted into a patient at a convenient location, and then navigated to a particular body tissue, body lumen, body cavity, hollow organ, or other region of interest. As another example, a scanning beam borescope may be navigated to a particular component of an automobile, instrument, machine, or other region of interest. Images acquired during navigation may help a user to know where the scanning beam device is, where the device is going, or otherwise guide or steer the navigation. During this time high frame rates may be desirable.

Then, once the scanning beam device reaches the region of interest, images of the region of interest may be acquired while the scanning beam image acquisition device is maintained substantially still, at block 227. It is often desirable to obtain relatively high quality images of the region of interest. As one example, in the case of a scanning beam endoscope, the images of the region of interest may be used for medical diagnosis or inspection. Maintaining the device substantially still generally helps to improve the quality of the images of the region of interest.

The acquired images may be characterized by frame rate and number of lines of image resolution. The "frame rate" is the number of individual images or frames acquired and displayed per unit time. The number of lines of image resolution is the number of "lines" of pixels per image or frame, where it is to be understood that for some types of scans the "lines" may be curves. For example, each spiral winding may represent two lines of image resolution on the display.

The same frame rate and number of lines of image resolution may be used to acquire images both while the device is moving and while it is substantially still. However there are certain drawbacks with this approach. For one thing, the acquired images may tend to be distorted if the device is moving too fast relative to the rate of image acquisition. Also, images acquired while the device is moving may tend to become "outdated" more rapidly than images acquired while the device is still. The distorted or outdated images may not accurately represent the actual position or surroundings of the device. As a result, the user may not accurately know where the device is or where it is going. This may tend to slow down navigation, result in navigating off course, or otherwise adversely affect navigation.

For another thing, it tends to be relatively more important for the images acquired of the region of interest to be of higher quality, for example number of lines of image resolution, compared to the images acquired during navigation. Also, the images acquired while the scanning beam device is substantially still tend not to become outdated as quickly, and may be displayed for longer periods of time. Since the scanning beam device is substantially still, image distortion due to movement also tends to be less.

In scanning beam image acquisition devices, where the scan is generally performed at a relatively constant scan rate, as in the case of an optical fiber vibrated at or around a resonant frequency (see e.g., FIG. 11), there is often a trade off between frame rate and image resolution. By way of example, consider the case of a cantilevered optical fiber moving in a spiral scan. A greater number of spiral windings may be used to increase the number of lines of image resolution. However, the additional spiral windings generally add to the amount of time needed to complete the scan, resulting in a decrease in the frame rate. Similarly, various other scanning beam devices may experience a trade off between frame rate and number of lines of image resolution. Generally, the more lines of resolution used in the scan, the longer it takes to complete the scan.

Figure 3:
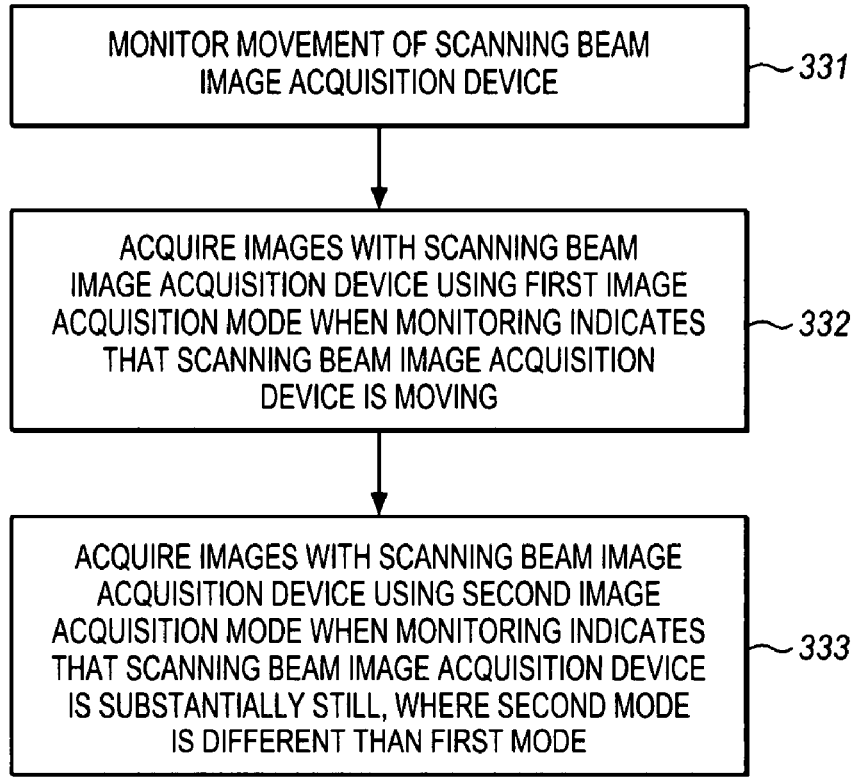
FIG. 3 is a block flow diagram of a method of acquiring images with a scanning beam image acquisition device using different image acquisition modes, according to embodiments of the invention.

In one or more embodiments of the invention, different modes of image acquisition may be used when a scanning beam device is moving and when it is substantially still. FIG. 3 is a block flow diagram of a method 330 of acquiring images with a scanning beam image acquisition device using different image acquisition modes, according to embodiments of the invention.

At block 331, movement of the scanning beam image acquisition device may be monitored. In embodiments of the invention, monitoring the movement may include sensing the movement with one or more sensors. As another option, in embodiments of the invention, monitoring the movement may include computing the movement from images acquired with the scanning beam image acquisition device. In various embodiments of the invention, the monitoring may be performed periodically or continuously throughout the method.

At block 332, when the monitoring indicates that the scanning beam image acquisition device is moving, images may be acquired with the scanning beam image acquisition device using a first image acquisition mode.

At block 333, when the monitoring indicates that the scanning beam image acquisition device is substantially still, images may be acquired with the scanning beam image acquisition device using a second image acquisition mode. As used herein, "substantially still" means moving less than 5 mm/sec. In various embodiments of the invention, the device may move even slower, such as, for example, less than 2 mm/sec, or less than 1 mm/sec. Additionally, as used herein unintentional jitter, mechanical vibration, or shaking due to uneasiness of the hand, when the device is intended to be substantially still, are encompassed by "substantially still".

The second image acquisition mode is different, in at least some way, than the first image acquisition mode. In embodiments of the invention, the first image acquisition mode may have a relatively higher frame rate than the second image acquisition mode. The relatively higher frame rate during movement may help to prevent the images from becoming distorted and/or outdated.

In embodiments of the invention, the second image acquisition mode may have a relatively higher number of lines of image resolution than the first image acquisition mode. The relatively higher number of lines of image resolution while the device is substantially still may help to allow high quality images to be acquired of the region of interest.

In embodiments of the invention, the first image acquisition mode may have a relatively higher frame rate than the second image acquisition mode, and the second image acquisition mode may have a relatively higher number of lines of image resolution than the first image acquisition mode. While the device is substantially still, the images tend not to become distorted and tend to become outdated more slowly and correspondingly a reduction in frame rate, if any, tends to be an acceptable compromise. Likewise, while the device is being navigated or moved, obtaining high quality images tends to be relatively less important and a reduction in number of lines of image resolution, if any, tends to be an acceptable compromise.

Additionally, or alternatively, other characteristics of the first and second modes may also optionally be different. For example, in one or more embodiments of the invention, a relatively larger field of view may optionally be used in the first image acquisition mode compared to that used in the second image acquisition mode. As another example, in one or more embodiments of the invention, a zoom factor of the scanning beam image acquisition device may be zoomed differently based on the image acquisition mode, for example to provide either more or less zoom when the device is moving than when it is still. Advantageously, this may help to allow the user to navigate based on a larger field of view of the surrounding environment. However, this is not required.

A particular method has been shown and described in order to illustrate certain concepts, although the scope of the invention is not limited to this particular method. In one aspect, certain operations may optionally be performed in different order and/or repeatedly. For example, the operations of block 332 and block 333 may be performed in reverse order. As another example, the method may switch back and forth between the operations of block 332 and block 333 throughout the method depending upon the monitored movement of the device. In another aspect, certain operations may optionally also be added to the method. For example, switching between modes may be conditioned upon a comparison of the monitored movement with one or more thresholds. As another example, three or more or a continuum of different image acquisition modes may be used based on different levels of movement. Many further modifications and adaptations may be made to the methods and are possible and will be apparent to those skilled in the art and having the benefit of the present disclosure.

Figure 4:
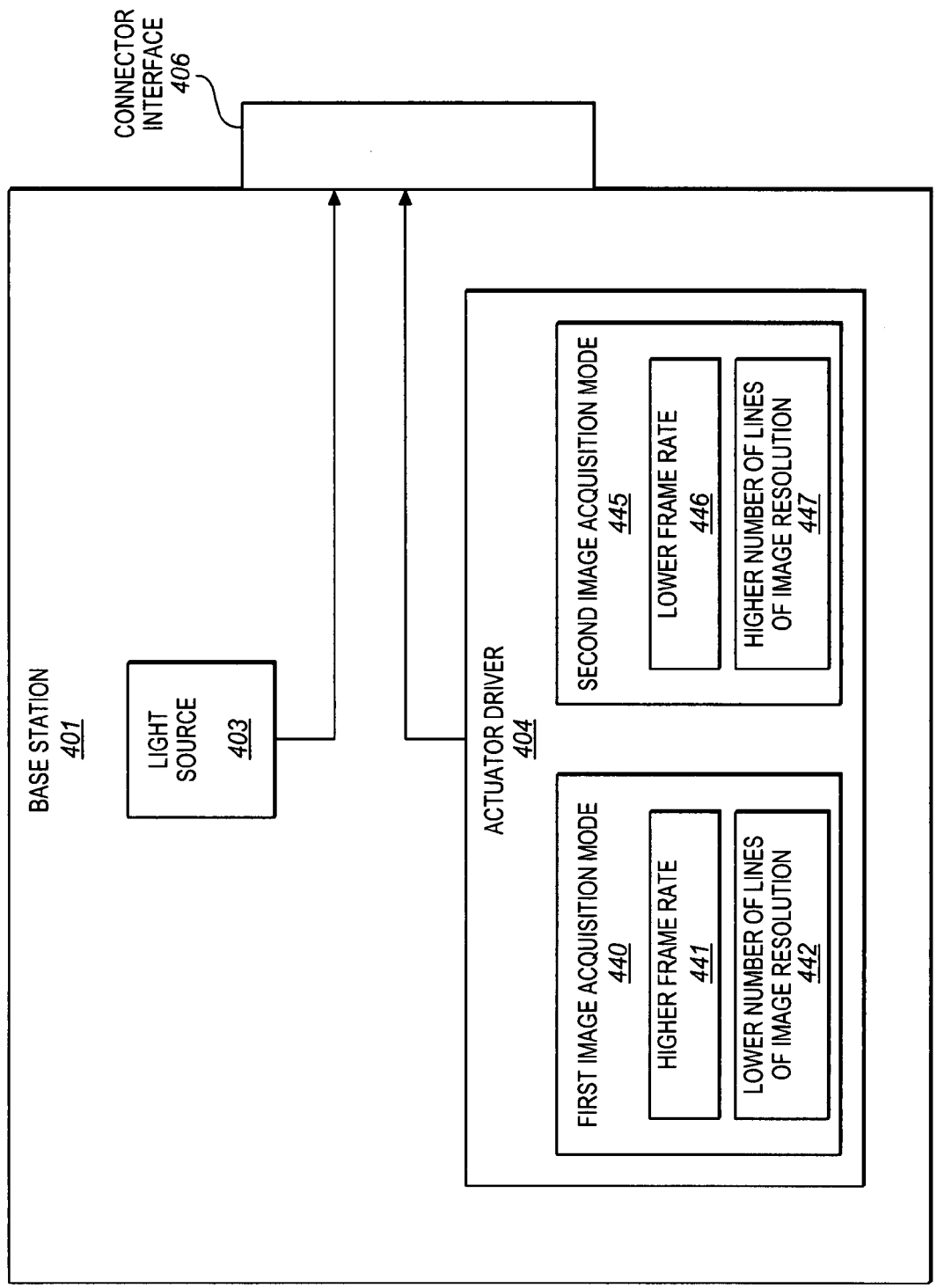
FIG. 4 is a block diagram of a portion of a base station having an actuator driver 404 with different image acquisition modes, according to embodiments of the invention.

FIG. 4 is a block diagram of a portion of a base station 401 having an actuator driver 404 with different image acquisition modes 440, 445, according to embodiments of the invention. Unless specified otherwise, the base station 401 may be similar to the base station 101 shown in FIG. 1. The discussion below will focus primarily on the different and/or additional characteristics of the base station 401.

The base station includes a connector interface 406. The connector interface may allow a scanning beam image acquisition device to be attached. The base station also includes a light source 403. The light source may provide light to a scanning beam image acquisition device through the connector interface.

The base station also includes an actuator driver 404, in accordance with embodiments of the invention. The actuator driver may be operable to provide actuator drive signals to an actuator of the scanning beam image acquisition device through the connector interface. The actuator driver may be operable to provide actuator drive signals according to a first image acquisition mode 440 responsive to an indication that the scanning beam image acquisition device is moving. The actuator driver may be operable to provide actuator drive signals according to a second image acquisition mode 445 responsive to an indication that the scanning beam image acquisition device is substantially still.

As shown, in one or more embodiments of the invention, the first image actuation mode may have a higher frame rate 441 and lower number of lines of image resolution 442. Likewise, the second image actuation mode may have a lower frame rate 446 and a higher number of lines of image resolution 447.

Different ways of implementing the first and second image acquisition modes are possible. In one or more embodiments of the invention, a first look-up table or other data structure stored in a memory may be used to store actuator drive signal values to implement the first image acquisition mode. Likewise, a second look-up table or other data structure may be used to store actuator drive signal values to implement the second mode.

Alternatively, in one or more embodiments of the invention, a first circuit, algorithm, or set of machine-readable instructions may be used to compute actuator drive signal values in real time to implement the first image acquisition mode. Likewise, a second circuit, algorithm, or set of machine-readable instructions may be used to compute actuator drive signal values in real time to implement the second mode. As another option, computation may be used to interpolate between stored values.

In one or more embodiments, the stored and/or computed actuator drive signal values for either or both of the modes may optionally be calibrated or otherwise adjusted prior to use. By way of example, different look-up tables or other data structures may be used to store different sets of calibration data for the different modes.

The actuator driver may cycle through the lookup tables or computations providing the actuator drive signal values. In some cases, the values after any optional calibration may be digital and may be provided to a digital-to-analog converter of the actuator driver. The actuator driver may also include one or more amplifiers to amplify the analog version of the actuator drive signals.

In one or more embodiments of the invention, the base station may optionally have a switch, button, knob, dial, setting, or other mechanism (not shown) to allow a user to override automatic switching between the first and second image acquisition modes. The mechanism may allow the user to force the actuator driver to use either the first mode or the second mode for image acquisition.

Now various different ways of monitoring movement of the scanning beam image acquisition device will be disclosed. In embodiments of the invention, one or more sensors may be used to sense movement of the scanning beam image acquisition device. Different approaches are possible.

Figure 5:
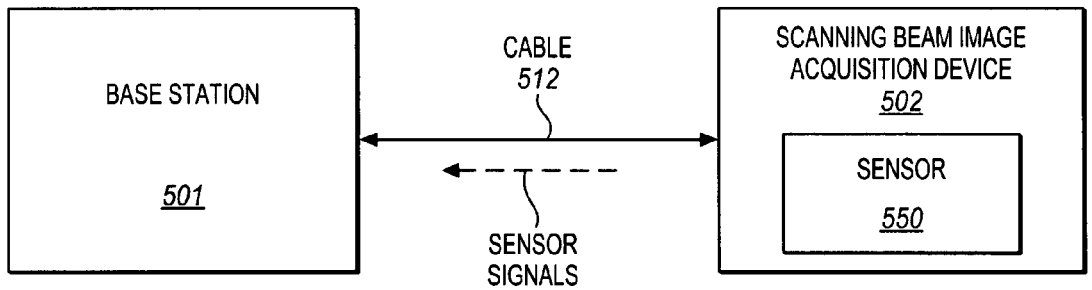
FIG. 5 is a block diagram showing a first approach for monitoring movement of a scanning beam image acquisition device by sensing the movement with a sensor that moves with the device, according to embodiments of the invention.

FIG. 5 is a block diagram showing a first approach for monitoring movement of a scanning beam image acquisition device 502 by sensing the movement with a sensor 550 that moves with the device, according to embodiments of the invention.

A scanning beam image acquisition system includes a base station 501 and the scanning beam image acquisition device 502. The sensor 550 is coupled with the scanning beam device. By way of example, the sensor may be contained within a housing of the scanning beam device or attached to an outside of the housing. As a result, the sensor may move with the scanning beam device.

In one or more embodiments of the invention, the sensor may include a small magnetic tracking device, although the scope of the invention is not so limited. Examples of suitable small magnetic tracking devices include, but are not limited to, the 1.3 mm and 0.3 mm magnetic sensors, which are commercially available from Ascension Technology Corporation, of Milton, Vt. However, the scope of the invention is not limited to these particular sensors. These sensors may be used with microBIRD® or other suitable electronics units (not shown) and DC magnetic field transmitters (not shown) also available from Ascension.

In operation, the DC magnetic field transmitter may generate a magnetic field. The sensor may sense the magnetic field and generate a corresponding sensor signal. As shown, the sensor signal may optionally be provided from the sensor to the base station through a cable 512. Alternatively, the sensor signal may be provided to the electronics unit or another component. The electronics unit or other component may optionally provide the sensor signal, or signal derived from the sensor signal, to the base station.

Either the other component, or the base station, or both, may compute the position and potentially the orientation of the sensor from the signal from the sensor. These computations may be performed in conventional ways. U.S. Patent Application 20070078334 presently assigned to Ascension discusses DC a magnetic-based position and orientation monitoring system for tracking medical instruments in greater detail.

Alternatively, rather than sensing the movement of the scanning beam image acquisition device directly, the movement of a cable coupling the scanning beam image acquisition device with the base station may be sensed. The motion of the cable may be sensed in different ways.

Figure 6:
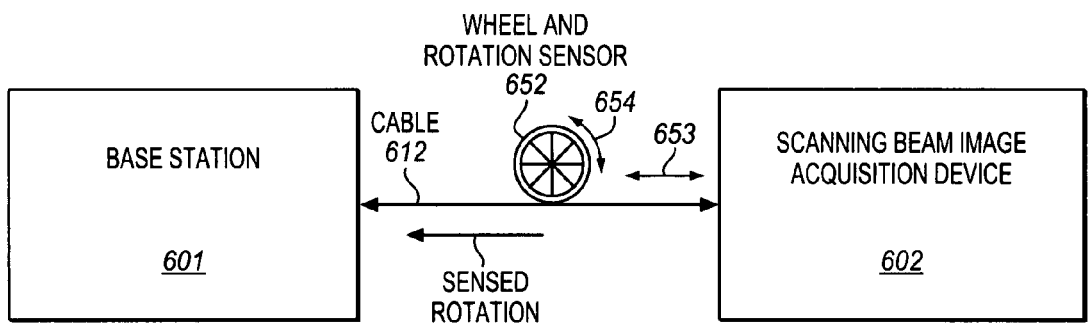
FIG. 6 is a block diagram showing a second approach for monitoring movement of a scanning beam image acquisition device by mechanically sensing movement of a cable with a wheel and associated rotation sensor, according to embodiments of the invention.

FIG. 6 is a block diagram showing a second approach for monitoring movement of a scanning beam image acquisition device 602 by mechanically sensing movement of a cable 612 with a wheel and associated rotation sensor 652, according to embodiments of the invention.

The scanning beam image acquisition device 602 is coupled with a base station 601 through a cable 612. Movement of the scanning beam device may result in movement of the cable as shown by arrow 653. The wheel is coupled with the cable and operable to be turned or rotated by movement of the cable, as shown by arrow 654. The rotation sensor may sense the rotation of the wheel.

The sensed rotation may be provided to the base station. The base station may estimate movement of the scanning beam image acquisition device based in part on the sensed rotation of the wheel. For example, the rate of rotation of the wheel may be multiplied by the circumference of the wheel to estimate the rate of movement of the scanning beam device.

Figure 7:
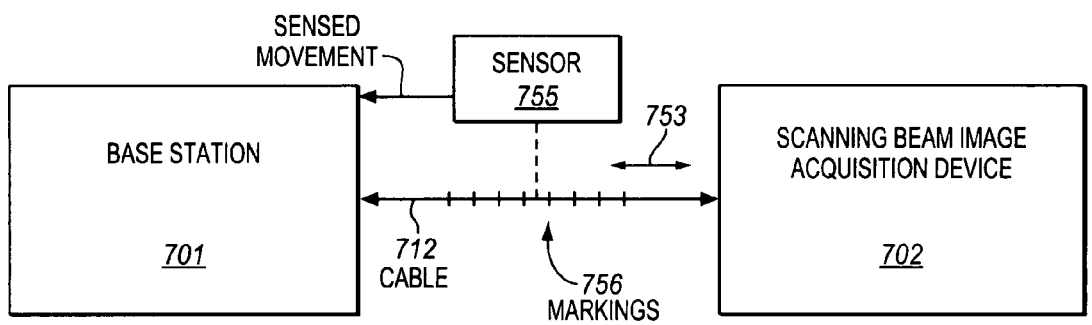
FIG. 7 is a block diagram showing a third approach for monitoring movement of a scanning beam image acquisition device by optically or magnetically sensing movement of a cable with a sensor, according to embodiments of the invention.

Mechanically sensing the motion of the wheel is not required. FIG. 7 is a block diagram showing a third approach for monitoring movement of a scanning beam image acquisition device 702 by optically or magnetically sensing movement of a cable 712 with a sensor 755, according to embodiments of the invention.

The scanning beam image acquisition device 702 is coupled with a base station 701 through a cable 712. Movement of the scanning beam device may result in movement of the cable as shown by arrow 753. The sensor is positioned relative to the cable to sense movement of the cable. As one example, the sensor may include an optical sensor to optically sense movement of the cable for example with a beam of light. As another example, the sensor may include a magnetic sensor to magnetically sense movement of the cable for example through a magnetic field.

As shown, in one or more embodiments, optical or magnetic markings or other position indicators 756 may optionally be included on the wheel to facilitate sensing. As one example, the markings may include evenly spaced lines, dots, or other markings. As another example, the markings may include unevenly spaced markings at known locations or known relative locations. Alternatively, words or other markings natively on the cable may be used to sense movement.

The sensor may provide signals representing the sensed movement of the cable to the base station. The base station may estimate movement of the scanning beam device based on the sensed movement of the cable.

Figure 8:
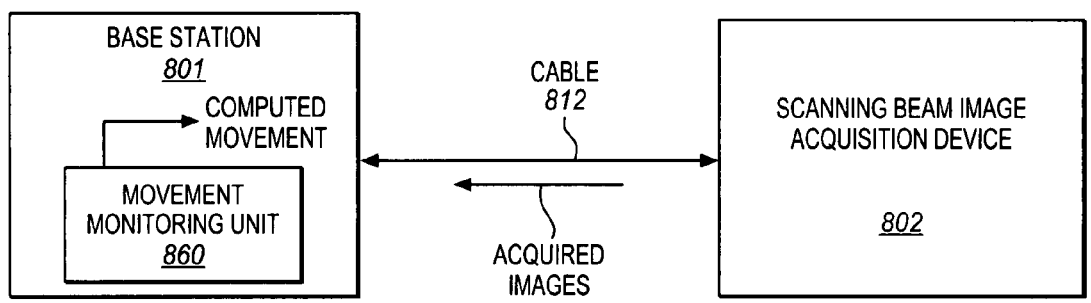
FIG. 8 is a block diagram showing a fourth approach for monitoring movement of a scanning beam image acquisition device by computing the movement from images acquired with the scanning beam image acquisition device, according to embodiments of the invention.

Sensing the movement with a sensor is not required. FIG. 8 is a block diagram showing a fourth approach for monitoring movement of a scanning beam image acquisition device 802 by computing the movement from images acquired with the scanning beam image acquisition device, according to embodiments of the invention.

As conventionally done, optical or electrical signals associated with images acquired with the scanning beam image acquisition device 802 may be provided to a base station 801 over a cable 812. The base station includes a movement monitoring unit 860. The movement monitoring unit may be implemented in hardware, software, or a combination of hardware and software. The movement monitoring unit may monitor movement of the scanning beam image acquisition device by computing the movement from the images acquired with the scanning beam image acquisition device.

In one or more embodiments of the invention, the movement may be computed using an optical flow technique. Various suitable optical flow techniques are known in the art. See e.g., the article "Systems and Experiment: Performance of Optical Flow Techniques", published in International Journal of Computer Vision, 12:1, 43-47 (1994), by J. L. Barron et al.

To further illustrate certain concepts, it may be helpful to consider a detailed example of one possible scanning fiber image acquisition device, how the device may be actuated, and how the device may in embodiments be operated at or around a resonant frequency.

Figure 9:
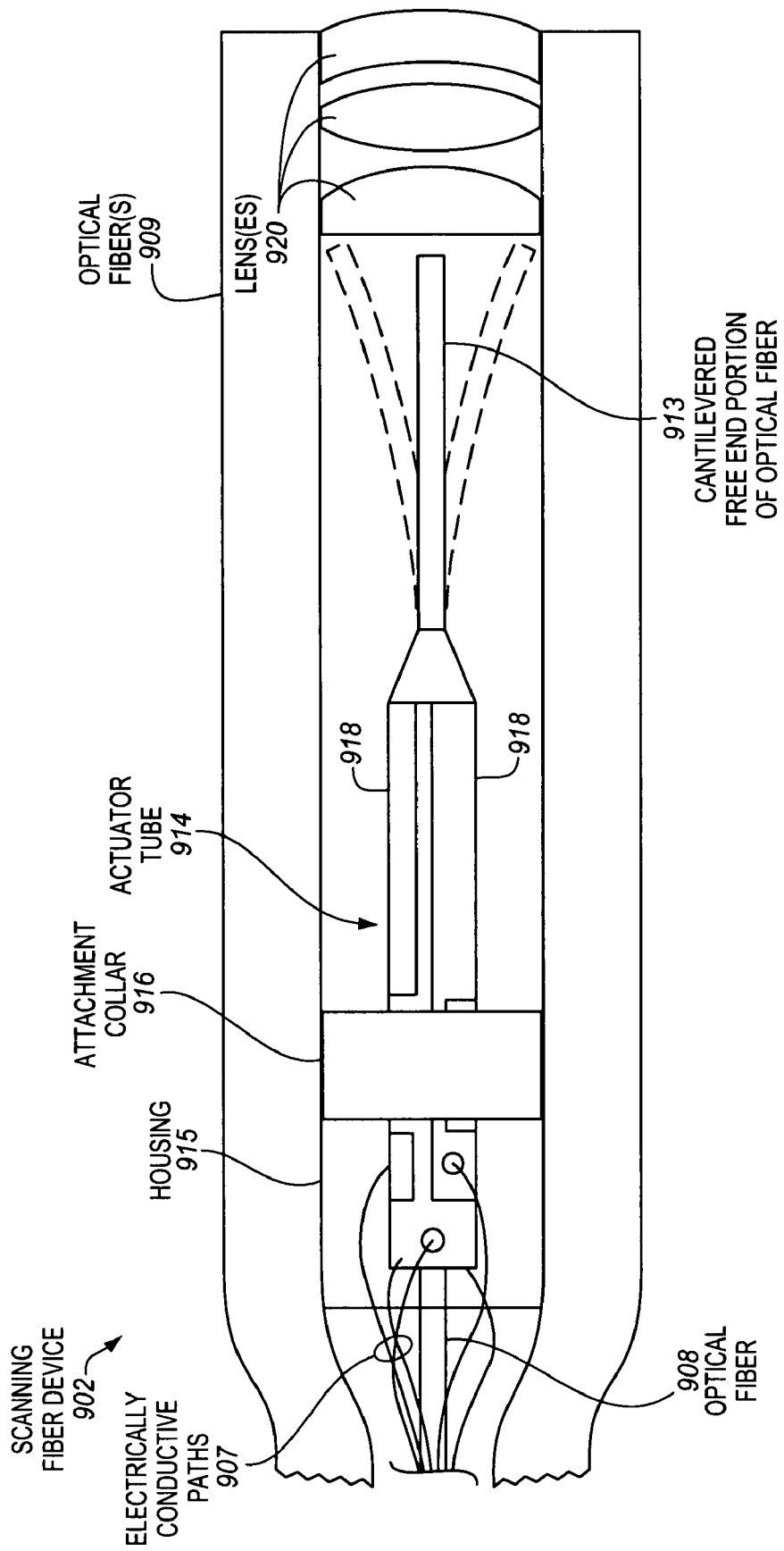
FIG. 9 is a cross-sectional side view of one possible example of a suitable scanning fiber device, according to embodiments of the invention.

FIG. 9 is a cross-sectional side view of one possible example of a suitable scanning fiber device 902, according to embodiments of the invention. This particular scanning fiber device is well suited for use as an endoscope or other relatively small device, although in other implementations the design and operation may vary considerably. The scope of the invention certainly is not limited to this particular device.

The scanning fiber device includes a housing 915. In one or more embodiments, the housing may be relatively small and hermetically sealed. For example, the housing may be generally tubular, have a diameter that is about 5 mm or less, and have a length that is about 20 mm or less. The housing typically includes one or more lenses 920. Examples of suitable lenses include those manufactured by Pentax Corporation, although other lenses may optionally be used.

As shown, in one or more embodiments, one or more optical fibers 909 may optionally be included, for example around the outside of the housing, to collect and convey backscattered light from the illumination spot back to one or more photodetectors, for example located in the base station. Alternatively, one or more photodetectors may be included at a distal tip of the scanning fiber device.

An actuator tube 914 is included in the housing and attached to the housing with an attachment collar 916. In one or more embodiments of the invention, the actuator tube may include a piezoelectric tube, such as, for example, of a PZT 5A material, although this is not required. Suitable piezoelectric tubes are commercially available from several sources including, but not limited to: Morgan Technical Ceramics Sales, of Fairfield, N.J.; Sensor Technology Ltd., of Collingwood, Ontario, Canada; and PI (Physik Instrumente) L.P., of Auburn, Mass. The actuator tube may be inserted through a tightly fitting generally cylindrical opening of the attachment collar.

A portion of a single optical fiber 908 is inserted through a generally cylindrical opening in the actuator tube. A cantilevered free end portion 913 of the optical fiber extends beyond an end of the actuator tube within the housing and may be attached to the end of the actuator tube. Other configurations are also possible. The cantilevered optical fiber is flexible and may be vibrated or moved by the actuator.

The actuator tube has electrodes 918 thereon. Wires or other electrically conductive paths 907 are electrically coupled with the electrodes to convey actuator drive signals to the electrodes. In one example embodiment of the invention, the actuator tube may include a piezoelectric tube having four, quadrant metal electrodes on an outer surface thereof to move the cantilevered optical fiber in two dimensions. Four paths may each be soldered to, or otherwise electrically coupled with, respective ones of the four electrodes. Responsive to the actuator drive signals, the four electrodes may cause the piezoelectric tube to vibrate or move the optical fiber in a two-dimensional scan, such as, for example, a spiral scan. In one or more embodiments, the piezoelectric tube may have an optional ground electrode on an inside surface thereof.

Figure 10:
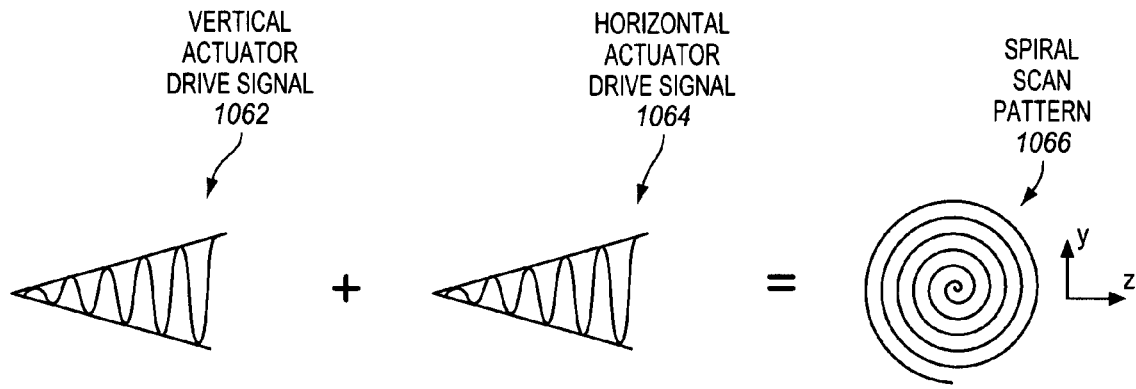
FIG. 10 shows an example pair of actuator drive signals that are operable to be applied to the electrodes of a scanning fiber device similar to that show in FIG. 9 in order to scan a cantilevered optical fiber in a spiral scan pattern, according to embodiments of the invention.

FIG. 10 shows an example pair of actuator drive signals 1062, 1064 that are operable to be applied to the electrodes of a scanning fiber device similar to that show in FIG. 9 in order to scan a cantilevered optical fiber in a spiral scan pattern 1066, according to embodiments of the invention. The pair of drive signals include a vertical actuator drive signal 1062 and a horizontal actuator drive signal 1064. By way of example, the vertical actuator drive signal may be $(y=a1(t)*\sin(wt+\theta))$ and the horizontal actuator drive signal may be $(z=a2(t)*\cos(wt))$, where $a1(t)$ and $a2(t)$ are potentially different amplitudes or voltages potentially varied as a function of time, w is 2*p*f, f is frequency, t is time, and θ is a phase shift. Typically, the horizontal and vertical actuator drive signals are about 90° out-of-phase, due to the sine and cosine. In a real system the phase difference may differ from 90° out-of-phase and this different may be adjusted with the phase shift θ.

Figure 11:
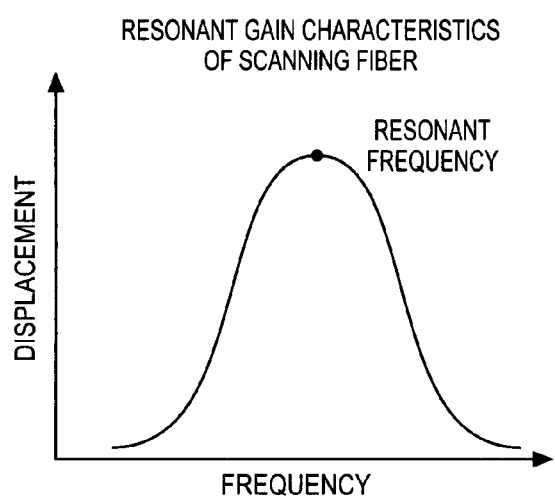
FIG. 11 is a graph of example resonant gain characteristics of a cantilevered optical fiber operated in a first mode of resonance.

FIG. 11 is a graph of example resonant gain characteristics of a cantilevered optical fiber operated in a first mode of resonance. Frequency of vibration of the cantilevered optical fiber is plotted on the horizontal axis versus displacement or deflection of the free distal end of the cantilevered optical fiber on the vertical axis.

The displacement increases around, and peaks at, a mechanical or vibratory resonant frequency. This is due to an increase in the resonant gain of the cantilevered optical fiber. In the illustration, the displacement has a relatively Gaussian dependency on frequency, with the greatest displacement occurring at the resonant frequency. In practice, there may be significant deviation from such a Gaussian dependency, although the displacement still typically peaks at the resonant frequency.

While the optical fiber may be vibrated at various frequencies, in practice the optical fiber is generally vibrated at or around, for example within a Q-factor of, its resonant frequency, or harmonics of the resonant frequency. As is known, the Q-factor is the ratio of the height of the resonant gain curve to the width of the curve. Due to the increased resonant gain, vibrating the optical fiber at or around the resonant frequency may help to reduce the amount of energy, or magnitude of the actuator drive signal, needed to achieve a given displacement, or perform a given scan.

Referring again to FIG. 10, the frequencies of each of the actuator drive signals are the same and are each generally constant. The equal frequencies of the actuator drive signals cause the cantilevered optical fiber to rotate in the spiral at the same generally constant frequency or number of revolutions per minute, often at or around the resonant frequency. Accordingly, each spiral winding takes about the same amount of time to complete. As a result, the more spiral windings in a scan, the longer time it takes to complete the scan.

The actuator drive signals also each have increasing amplitude. The amplitudes of the horizontal and vertical actuator drive signals are generally roughly equal to achieve a circular spiral, although in a real system the amplitudes may be unequal. The "diameter" of the spiral increases as the amplitudes of the drive signals increase. A faster ramp or rate of increase in the amplitudes of the drive signals may result in a faster increase in spiral diameter or fewer spiral windings to achieve a maximum spiral diameter. The maximum diameter of the spiral generally coincides with the maximum amplitudes of the drive signals. The maximum diameter of the spiral may correspond to a maximum field of view. In one or more embodiments, a faster ramp of amplitudes may be used for a first image acquisition mode to achieve the same maximum spiral diameter as used in a second image acquisition mode (same field of view) but using less spiral turns, and as a result having a higher frame rate and a lower image resolution.

For an optical fiber vibrated at constant frequency, the frame rate may be decreased by increasing the number of spiral windings. Alternatively, the frame rate may be increased by decreasing the number of spiral windings. As previously discussed, the number of lines of image resolution may be increased by increasing the number of spiral windings, or the number of lines of image resolution may be decreased by decreasing the number of spiral windings. For example, there may be two lines of image resolution per winding of the spiral.

Figure 12:
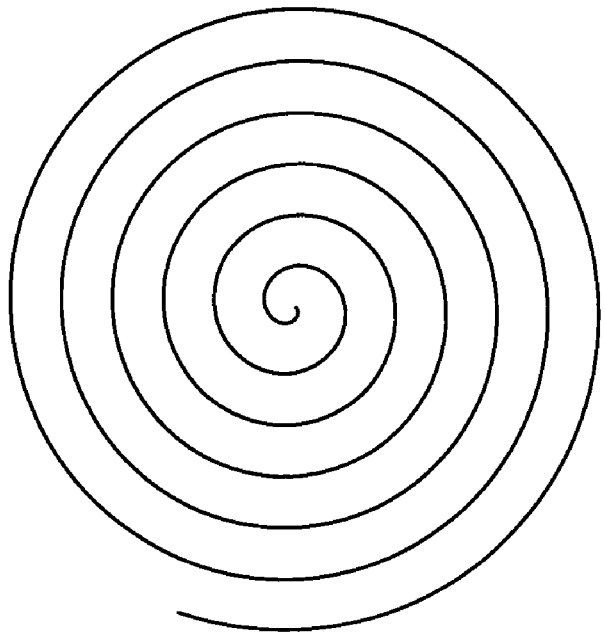
FIG. 12 shows examples of a first spiral scan suitable for a first image acquisition mode and a second spiral scan suitable for a second image acquisition mode, according to embodiments of the invention.
Figure 12:
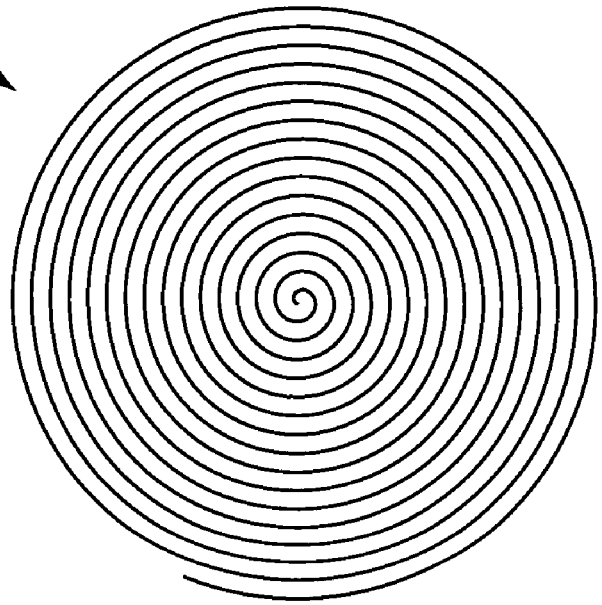

FIG. 12 shows examples of a first spiral 1268 suitable for a first image acquisition mode to be used when a scanning beam device is moving and a second spiral 1269 suitable for a second image acquisition mode to be used when a scanning beam device is substantially still, according to embodiments of the invention.

Notice that the second spiral has a greater number of spiral windings than the first spiral. As previously discussed, this may provide a relatively greater frame rate for the first image acquisition mode and a relatively greater number of lines of image resolution for the second image acquisition mode.

For ease of illustration, relatively few spiral windings have been shown, although often more spiral windings may be used. As one particular example, about 150 spiral windings (300 lines of image resolution) may be used for the first image acquisition mode, whereas about 500 spiral windings (1000 lines of image resolution) may be used for the second image acquisition mode. If a cantilevered optical fiber having a resonant frequency of about 5 kHz is used to scan the beam, this may result in a frame rate of about 21 Hz (30 ms to expand the spiral and 17 ms to actively dampen and settle) for the first image acquisition mode. The frame rate may be about 8.5 Hz (100 ms to expand the spiral and 17 ms to actively dampen and settle) for the second image acquisition mode. However the scope of the invention is not limited to this particular example, which is only illustrative.

In the illustration, the spirals have about the same maximum diameter. This may provide about the same field of view. Alternatively, either spiral may optionally have a larger diameter or field of view.

In one or more embodiments of the invention, each of the first and second spirals may be created by providing actuator drive signals similar to those shown in FIG. 10. However, a relatively faster voltage ramp may be used to generate the first spiral compared to that used to generate the second spiral.

In one or more embodiments of the invention, a comparison with one or more thresholds may be used to determine when to switch between first and second image acquisition modes. A single threshold may optionally be used. For example, the first mode may be used if monitored movement is greater than the threshold, and the second more may be used if monitored movement is less than or equal to the threshold. However, rapid switching back-and-forth or thrashing may potentially occur.

One approach to help reduce such rapid switching back-and-forth between modes, according to one or more embodiments of the invention, may include determining that a waiting time has elapsed before allowing switching between the first and second image acquisition modes. As one example, after crossing a threshold, a counter may start keeping track of time. A comparison may be made periodically whether the elapsed time is greater than a waiting time. The image acquisition mode may not be changed until after a determination that the waiting time has elapsed. As another example, after crossing a threshold, an image acquisition mode may be changed right away. A counter may then start keeping track of time. A comparison may be made periodically whether the elapsed time is greater than a waiting time. The image acquisition mode may not be changed again until after a determination that the waiting time has elapsed. Another approach to help reduce such rapid switching back-and-forth between modes, according to one or more embodiments of the invention, may include using multiple different thresholds, as discussed next.

Figure 13:
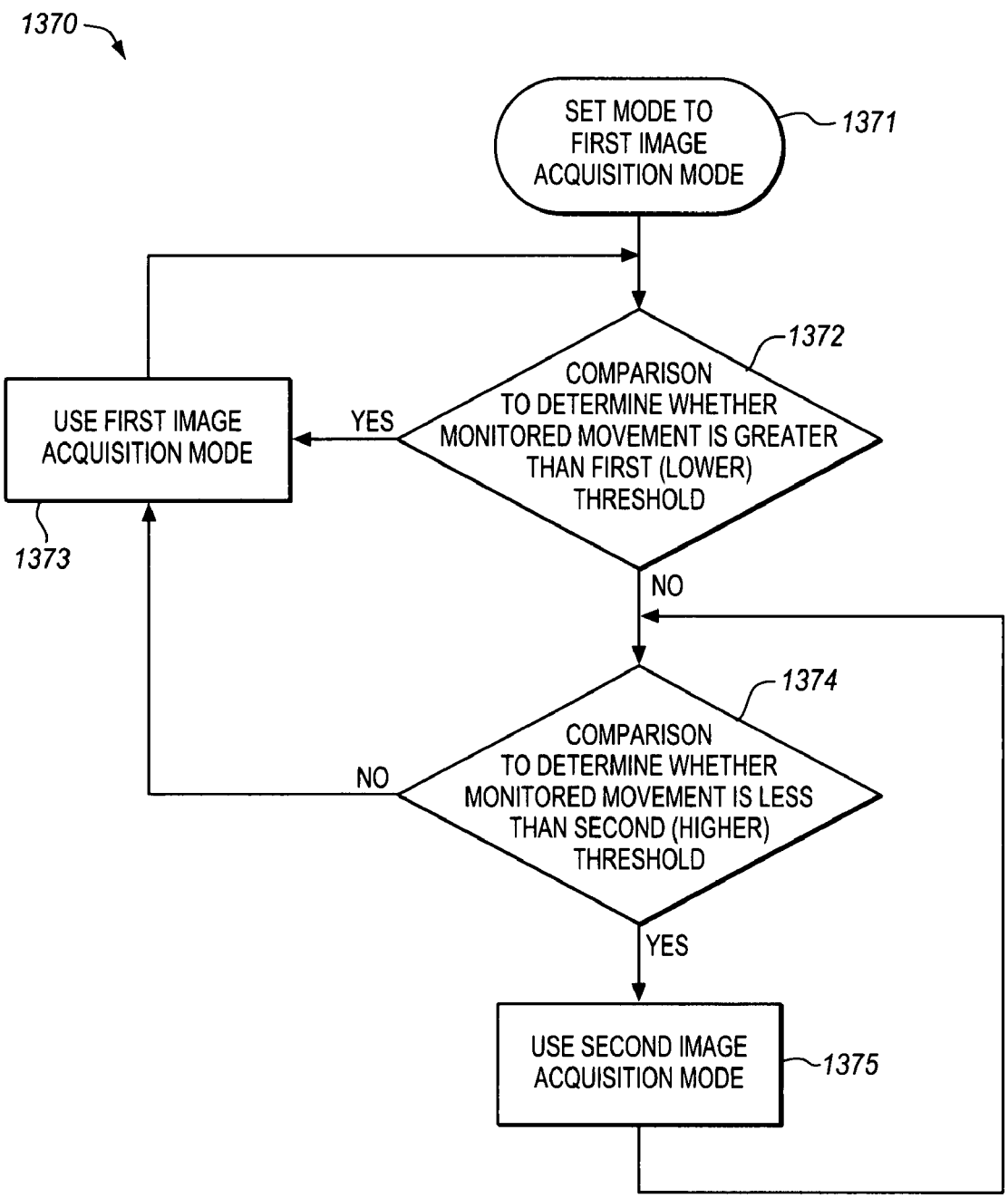
FIG. 13 is a block flow diagram of a method of determining whether to use a first image acquisition mode or a second image acquisition mode to acquire images, according to embodiments of the invention.

FIG. 13 is a block flow diagram of a method 1370 of determining whether to use a first image acquisition mode or a second image acquisition mode to acquire images, according to embodiments of the invention. At block 1371, a mode used for image acquisition may initially be set to a default mode, such as, for example, the first image acquisition mode, since it is common to start out navigating.

Then, at block 1372, a comparison may be used to determine whether the monitored movement is greater than a first, lower threshold. By way of example, the first, lower threshold may be 1 mm/sec.

If "yes" is the determination, then the method may advance to block 1373. At block 1373, the first image acquisition mode may be used to acquire images. The method may then revisit block 1372.

Alternatively, if "no" is the determination at block 1372, then the method may advance to block 1374. At block 1374, another comparison may be used to determine whether the monitored movement is less than a second, higher threshold. The second, higher threshold may be higher than the first threshold. By way of example, the second, higher threshold may be 2 mm/sec.

If "no" is the determination at block 1374, the method may advance to block 1373. Thereafter, the method may revisit block 1372, as previously described. Alternatively, if "yes" is the determination at block 1374, then the method may advance to block 1375. At block 1375, the second image acquisition mode may be used to acquire images. The method may then revisit block 1374.

Advantageously, such use of two or more different thresholds in this way may help to create a "hysteresis" in the mode switching process, which may help to reduce rapidly switching back-and-forth between modes. However the use of two or more different thresholds is not required.

In the description above, for the purposes of explanation, numerous specific details have been set forth in order to provide a thorough understanding of the embodiments of the invention. The particular embodiments described are not provided to limit the invention but to illustrate it. Embodiments may be practiced without some of these specific details. Furthermore, modifications may be made to the embodiments disclosed herein, such as, for example, to the configurations, functions, and manner of operation, of the components of the embodiments. All equivalent relationships to those illustrated in the drawings and described in the specification are encompassed within embodiments of the invention. The scope of the invention is not to be determined by the specific examples provided above but rather by the claims below.

It should also be appreciated that reference throughout this specification to "one embodiment", "an embodiment", or "one or more embodiments", for example, means that a particular feature may be included in the practice of the invention. Similarly, it should be appreciated that in the description various features are sometimes grouped together in a single embodiment, Figure, or description thereof for the purpose of streamlining the disclosure and aiding in the understanding of various inventive aspects. This method of disclosure, however, is not to be interpreted as reflecting an intention that the invention requires more features than are expressly recited in each claim. Rather, as the following claims reflect, inventive aspects may lie in less than all features of a single disclosed embodiment. Thus, the claims following the Detailed Description are hereby expressly incorporated into this Detailed Description, with each claim standing on its own as a separate embodiment of the invention.

What is claimed is:

1. A method comprising:
   monitoring movement of a scanning beam image acquisition device;
   acquiring images with the scanning beam image acquisition device using a first image acquisition mode when the monitoring indicates that the scanning beam image acquisition device is moving; and
   acquiring images with the scanning beam image acquisition device using a second image acquisition mode when the monitoring indicates that the scanning beam image acquisition device is substantially still, wherein the second image acquisition mode is different than the first image acquisition mode.

2. The method of claim 1, wherein a frame rate of the first image acquisition mode is higher than a frame rate of the second image acquisition mode.

3. The method of claim 1, wherein a number of lines of image resolution of the first image acquisition mode is lower than a number of lines of image resolution of the second image acquisition mode.

4. The method of claim 1, wherein a frame rate of the first image acquisition mode is greater than a frame rate of the second image acquisition mode, and wherein a number of lines of image resolution of the first image acquisition mode is less than a number of lines of image resolution of the second image acquisition mode.

5. The method of claim 1:
   wherein acquiring the images using the first image acquisition mode comprises scanning a beam in a first spiral having a first number of windings;
   wherein acquiring the images using the second image acquisition mode comprises scanning the beam in a second spiral having a second number of windings; and
   wherein the second number of windings is greater than the first number of windings.

6. The method of claim 1, wherein monitoring the movement comprises sensing the movement with a sensor.

7. The method of claim 6, wherein sensing the movement comprises sensing the movement with a sensor that moves with the scanning beam image acquisition device.

8. The method of claim 7, wherein sensing the movement with the sensor that moves with the scanning beam image acquisition device comprises sensing the movement with a miniature magnetic tracking device.

9. The method of claim 6, wherein sensing the movement comprises sensing the movement of a cable coupling the scanning beam image acquisition device with a base station.

10. The method of claim 1, wherein monitoring the movement comprises computing the movement from images acquired with the scanning beam image acquisition device.

11. The method of claim 1, further comprising comparing monitored movement with at least one threshold.

12. The method of claim 11, wherein comparing the monitored movement with the at least one threshold comprises comparing the monitored movement with two or more different thresholds, wherein the two or more different thresholds are operable to reduce rapid switching back and forth between the first and second modes.

13. The method of claim 11, further comprising determining that a waiting time has elapsed before switching between the first and second image acquisition modes.

14. The method of claim 1, wherein acquiring the images with the scanning beam image acquisition device using the first and second modes comprises acquiring the images with a scanning fiber image acquisition device.

15. The method of claim 14, wherein acquiring the images with the scanning beam image acquisition device using the first and second modes comprises vibrating a cantilevered optical fiber within a Q-factor of a resonant frequency.

16. The method of claim 1, further comprising a user overriding automatic switching between the first and second image acquisition modes and forcing image acquisition to be performed with only one of the first and second modes.

17. The method of claim 1, further comprising inserting the scanning beam image acquisition device into a patient.

18. An apparatus comprising:
   a connector interface to allow a scanning beam image acquisition device to be attached;
   a light source to provide light to the scanning beam image acquisition device through the connector interface; and
   an actuator driver operable to provide actuator drive signals to an actuator of a scanning beam image acquisition device through the connector interface,
   wherein the actuator driver is operable to provide the actuator drive signals according to a first image acquisition mode responsive to an indication that the scanning beam image acquisition device is moving, and
   wherein the actuator driver is operable to provide actuator drive signals according to a second image acquisition mode responsive to an indication that the scanning beam image acquisition device is substantially still, and
   wherein the second mode is different than the first mode.

19. The apparatus of claim 18, wherein a frame rate of the first image acquisition mode is higher than a frame rate of the second image acquisition mode.

20. The apparatus of claim 18, wherein a number of lines of image resolution of the first image acquisition mode is lower than a number of lines of image resolution of the second image acquisition mode.

21. The apparatus of claim 18, wherein a frame rate of the first image acquisition mode is greater than a frame rate of the second image acquisition mode, and wherein a number of lines of image resolution of the first image acquisition mode is less than a number of lines of image resolution of the second image acquisition mode.

22. The apparatus of claim 18:
   wherein the actuator drive signals according to the first mode are operable to cause the scanning beam image acquisition device to scan a beam in a first spiral having a first number of windings;
   wherein the actuator drive signals according to the second mode are operable to cause the scanning beam image acquisition device to scan a beam in a second spiral having a second number of windings; and
   wherein the second number of windings is greater than the first number of windings.

23. The apparatus of claim 18, further comprising a sensor to sense movement of the scanning beam image acquisition device.

24. The apparatus of claim 23, wherein the sensor comprises a sensor attached to the scanning beam image acquisition device.

25. The apparatus of claim 24, wherein the sensor comprises miniature magnetic tracking device.

26. The apparatus of claim 23, wherein the sensor comprises a sensor positioned relative to a cable coupling the scanning beam image acquisition device with the connector interface to sense movement of the cable.

27. The apparatus of claim 18, further comprising a movement monitoring unit to monitor movement of the scanning beam image acquisition device by computing movement from images acquired with the scanning beam image acquisition device.

28. The apparatus of claim 18, further comprising a mechanism to allow a user to force the actuator driver to use either the first mode or the second mode.

29. The apparatus of claim 18, wherein the first and second image acquisition modes each comprise a different set of one or more look-up tables in memory.

30. The apparatus of claim 18, wherein the first and second image acquisition modes comprise different algorithms implemented in instructions stored on a machine-readable medium, circuitry, or a combination thereof.

* * * * *